United States Patent
Fox et al.

(10) Patent No.: US 8,618,120 B2
(45) Date of Patent: Dec. 31, 2013

(54) SYNERGISTIC COMBINATIONS OF VR-1 ANTAGONISTS AND COX-2 INHIBITORS

(75) Inventors: Alyson Fox, Horsham (GB); Mark Nash, Horsham (GB); Bindi Sohal, Horsham (GB); Elliot Lilley, Horsham (GB)

(73) Assignee: Novartis AG, Basel (CH)

( * ) Notice: Subject to any disclaimer, the term of this patent is extended or adjusted under 35 U.S.C. 154(b) by 765 days.

(21) Appl. No.: 12/452,519

(22) PCT Filed: Jul. 16, 2008

(86) PCT No.: PCT/EP2008/059296
§ 371 (c)(1),
(2), (4) Date: Jan. 5, 2010

(87) PCT Pub. No.: WO2009/010529
PCT Pub. Date: Jan. 22, 2009

(65) Prior Publication Data
US 2010/0144740 A1    Jun. 10, 2010

(30) Foreign Application Priority Data
Jul. 18, 2007    (EP) .................................... 07112679

(51) Int. Cl.
*A61K 31/517*    (2006.01)
*A61K 31/195*    (2006.01)
*A61K 31/196*    (2006.01)

(52) U.S. Cl.
USPC ..................................... 514/266.31; 514/567

(58) Field of Classification Search
USPC ............................................ 514/266.31, 567
See application file for complete search history.

(56) References Cited

U.S. PATENT DOCUMENTS

2007/0032500 A1    2/2007    Sun

FOREIGN PATENT DOCUMENTS

| EP | 1 967 519 | 9/2008 |
| WO | WO 02/076946 | 10/2002 |
| WO | WO 2004/056394 | 7/2004 |
| WO | WO 2005/120510 | 12/2005 |
| WO | WO 2006/124753 | 11/2006 |
| WO | WO 2007/074916 | 7/2007 |

OTHER PUBLICATIONS

Chawla et al., "Challenges in Polymorphism of Pharmaceuticals," CRIPS, Jan.-Mar. 2004, vol. 5, No. 1, pp. 9-12.*
Newman et al., "Solid-state analysis of the active pharmaceutical ingredient in drug products," DDT, Oct. 2003, vol. 8, No. 9, pp. 898-905.*
Ezio Tubaro et al., "Impact on the Bowel of Amtolmetin Guacyl, a New Gastroprotective Non-Steroidal Anti-Inflammatory Drug" European Journal of Pharmacology 467:173-183, 2003.
Kk Jain, "A Guide to Drug Evaluation for Chronic Pain" Emerging Drugs 5:241-257, 2000.

* cited by examiner

*Primary Examiner* — Sreeni Padmanabhan
*Assistant Examiner* — Jody Karol
(74) *Attorney, Agent, or Firm* — Michael G. Smith

(57) ABSTRACT

A synergistic combination of a vanilloid receptor VR-1 antagonist and an NSAID or a pharmaceutically acceptable salt or solvate of either or both compounds thereof.

2 Claims, 3 Drawing Sheets

SYNERGISTIC COMBINATIONS OF VR-1 ANTAGONISTS AND COX-2 INHIBITORS

The present invention relates to combinations of a vanilloid receptor (VR-1, TRPV1 or capsaicin receptor) antagonist and a non-steroidal anti-inflammatory drug (NSAID), such as a COX-2 inhibitor, for use in the treatment of disorders mediated by VR-1.

WO2004056394 describes combinations of VR-1 antagonists and NSAIDs, such as COX-2 inhibitors. The application discloses the ability of the VR-1 antagonist in the combination to reduce the required therapeutic dose of the NSAID and thereby reducing the propensity for any side effects. The application does not disclose any combinations where a synergistic or supra-additive effect is achieved between the two components. Thus, there is a need for improved therapeutic agents which can provide effective treatment at reduced doses with minimum side effects.

The present inventors have found that certain ratios of vanilloid VR-1 antagonists in combination with an NSAID, such as a COX-2 inhibitor, surprisingly interact in a synergistic manner to provide a particularly beneficial effect in the treatment of VR-1 mediated disorders, such as pain, and in alleviating the symptoms associated therewith. The agents may be administered simultaneously, sequentially or separately. This synergy allows a reduction in the prospective dose required of each compound, leading to a reduction in the side effects and enhancement of the clinical utility of the compounds.

Figure 1:
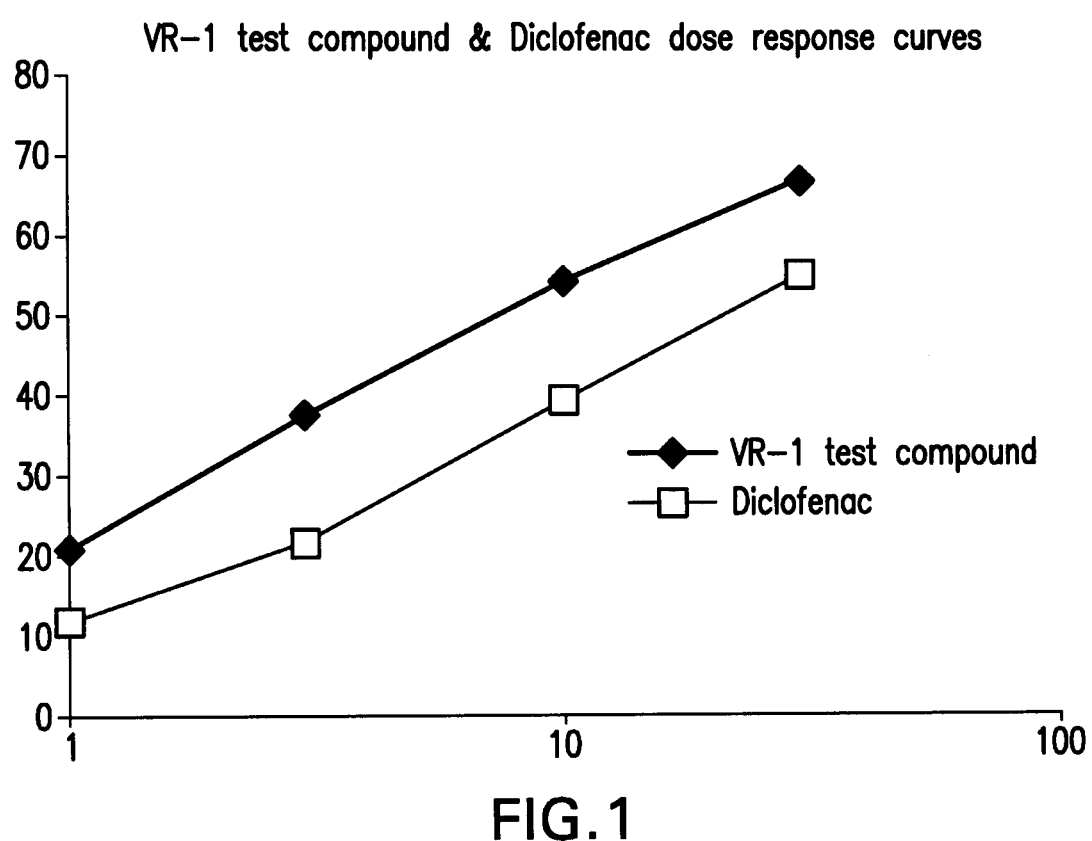
FIG. 1: Reversal of acute mechanical hyperalgesia induced by intraplantar FCA injection by oral administration of a vanilloid receptor VR-1 antagonist or diclofenac alone, where VR-1 test compound refers to the VR-1 antagonist 4-(7-Hydroxy-2-isopropyl-4-oxo-4H-quinazolin-3-yl)-benzonitrile.

Non-steroidal anti-inflammatory drugs (NSAIDS) are already used for the treatment of conditions associated with pain and in alleviating the symptoms associated therewith. However, significant side effects such as, inter alia, gastrointestinal erosion and renal impairment limit their use. The combination of the present invention is perceived to be particularly beneficial since such combinations allow an increased alleviation of conditions associated with disorders such as pain and their associated symptoms without compromising the therapeutic benefit.

The combinations of the present invention may also facilitate the attainment of the same level of alleviation of conditions associated with pain and their associated symptoms as higher doses of solely administered NSAIDS by using lower doses of NSAIDS in combination with the VR-1 receptor antagonists and thereby lowering the risk of significant side effects associated with NSAID use.

The combinations of the present invention may suitably comprise a sub-maximal amount of a vanilloid receptor VR-1 antagonist or an NSAID, such as a COX-2 inhibitor. Such compositions are indicated to provide a beneficial effect on pain and the conditions associated therewith.

When used herein the term 'sub-maximal' amount of a vanilloid receptor VR-1 antagonist or an NSAID, such as a COX-2 inhibitor means an amount lower than the appropriate non-combination dose for the active agent in question, as described or referred to in reference texts such as the British National Formulary (BNF), British and US Pharmacopoeias, Remington's Pharmaceutical Sciences (Mack Publishing Co.), Martindale The Extra Pharmacopoeia (London, The Pharmaceutical Press). A suitable sub-maximal dose is less than 100% and typically within the range of from 5-95% of the appropriate non-combination dose for the active agent in question, for example 75%, 80%, 90% or 95% of the appropriate non-combination dose for the active agent in question.

In particular, lowering the dose of the NSAID, such as COX-2 inhibitor, by the use of a sub-maximal dosage, in the presence of a full dose of a vanilloid receptor VR-1 antagonist also has the benefit of reducing side effects associated with NSAID use.

Similarly, potential side-effects associated with VR-1 antagonists, for example hyperthermia (Gawa et al., J Neurosci. Vol 27, No 13 pp 3366-3374, 2007), may be reduced by using a sub-maximal dosage of VR-1 antagonist in combination with a synergistic dose of the NSAID, such as a COX-2 inhibitor.

Drug efficacy may be assessed using a variety of pre-clinical acute and chronic somatic pain models such as, but not limited to, the carrageenan model (Guilbaud G. & Kayser V. Pain 28 (1987) 99-107) for acute inflammatory pain, the FCA model (Freund's Complete Adjuvant) (Hay et al., Neuroscience Vol 78, No 3 pp 843-850, 1997) for acute and chronic inflammatory pain, or the CCI model (Chronic Constriction Injury) (Bennett, G. J. & Xie. Y. K. (1988) Pain, 33: 87-107) for neuropathic pain. Effects on visceral pain can be assessed using preclinical models such as the mustard oil model (Laird et al., Pain Vol 92, No 3 pp 335-342), chemical- or mechanical-induced inflammatory visceral hyperalgesia models (Burton and Gebhart Brain Res Vol 672, No 1-2 pp 77-82) or stress-induced visceral hyperalgesia models (Schwetz et al., Vol 286, No 4 ppG 683-691).

Thus, as a first aspect, the present invention provides a synergistic combination of a vanilloid receptor VR-1 antagonist and an NSAID, such as a COX-2 inhibitor or a pharmaceutically acceptable salt or solvate of either or both compounds thereof.

It will be appreciated that reference to treatment is intended to include prophylaxis as well as the alleviation of established symptoms.

According to another aspect of the invention, there is provided the use of a vanilloid receptor VR-1 antagonist or a pharmaceutical acceptable derivative thereof for the manufacture of a medicament for the treatment of VR-1 mediated disorders, such as pain and the alleviation of symptoms associated thereof, in synergistic combination with an NSAID, such as a COX-2 inhibitor, or a pharmaceutical acceptable derivative thereof.

As a further or alternative aspect of the invention, there is provided the use of an NSAID, such as a COX-2 inhibitor, or a pharmaceutical acceptable derivative thereof for the manufacture of a medicament for the treatment of VR-1 mediated disorders, such as pain and the alleviation of symptoms associated thereof, in synergistic combination with a vanilloid receptor VR-1 antagonist or a pharmaceutical acceptable derivative thereof.

Compounds with biological activity as VR-1 antagonists are indicated to be useful in the treatment and/or prophylaxis of VR-1 mediated disorders, particularly the treatment or prevention of chronic pain with an inflammatory component such as rheumatoid arthritis; bone and joint pain (osteoarthritis); post-surgical or trauma pain including dental pain e.g. following third molar extraction, post mastectomy pain and pain associated with sprains or fractures; musculo-skeletal pain such as fibromyalgia; myofascial pain syndromes; headache, including migraine, acute or chronic tension headache, cluster headache, temporomandibular pain, and maxillary sinus pain; ear pain; episiotomy pain; burns, and especially primary hyperalgesia associated therewith; deep and visceral pain, such as heart pain, muscle pain, eye pain, orofacial pain, abdominal pain, gynaecological pain, such as dysmenorrhoea, and labour pain; hemorrhoids; pain associated with the urogenital tract such as cystitis and vulvadynia; chronic pain associated with nerve injury and/or diseases affecting the nervous system, such as neuropathic pain associated with post-herpetic neuralgia, diabetic neuropathy, chemotherapy-induced neuropathy, amputations ("phantom limb pain"), nerve entrapment and brachial plexus avulsions, low back pain, sciatica and ankylosing spondylitis, reflex sympathetic dystrophy and other chronic nerve injuries; complex regional pain syndromes; Glossodynia or burning mouth syndrome; central nervous system pain, such as pain due to spinal cord or brain stem damage, multiple sclerosis or stroke; gout; scar pain; pain associated with carcinoma, often referred to as cancer pain; pain associated with viral (e.g. HIV)-induced neuropathy, alcohol and narcotic abuse; pain and other symptoms associated with sun or UV burn, exposure to VR1 agonist (e.g. capsaicin, acid, tear gas, noxious heat or pepper spray), snake, spider or insect bite and jellyfish sting.

VR-1 antagonists used in accordance with the invention are useful for treating gastrointestinal disorders including those associated with gastrointestinal hypersensitivity, visceral pain and/or altered motor responses (including electrolyte/water secretion) such as functional bowel disorders and functional gastrointestinal disorders, including irritable bowel syndrome (IBS), functional dyspepsia, heartburn, non-erosive reflux disease, intestinal pseudo-obstruction, functional abdominal bloating, and functional abdominal pain; other conditions associated with visceral hypersensitivity including gastro-oesophageal reflux disease and emesis, oesophagitis, post-operative visceral pain, post-operative ileus, visceral smooth muscle spasms, ulcerative colitis, Crohn's disease, ulcers, chronic constipation, diarrhea, early satiety, epigastric pain, nausea, vomiting, burbulence, anal incontinence, faecal urgency and rectal hypersensitivity, gastroparesis, e.g. diabetic gastroparesis, pancreatitis and Hirschsprung's disease.

Urinary incontinence ("UI") or overactive bladder to be treated with VR-1 antagonists in accordance with the invention is a broad term that covers a range of disorders and symptoms including urge UI, stress UI, mixed urge/stress UI, neurogenic UI, bladder detrusor hyperreflexia (neurogenic detrusor overactivity), detrusor instability (idiopathic detrusor overactivity), decreased bladder compliance, weakness of urethal sphincter, urinary outlet obstruction, interstitial cystitis, nephritis, uveitis, sensory urgency, motor urgency, nocturia, and bladder-related visceral pain.

VR-1 antagonists are also useful as agents for the therapy of hyperreactive, inflammatory or obstructive airways diseases including asthma, inflammatory airways disease, e.g. chronic obstructive pulmonary or airways disease (COPD or COAD), adult respiratory distress syndrome (ARDS), chronic bronchitis, pneumoconiosis, e.g. aluminosis, anthracosis, asbestosis, chalicosis, ptilosis, siderosis, silicosis, tabacosis, byssinosis; rhinitis including allergic rhinitis such as seasonal and perennial rhinitis, and non-allergic rhinitis; cough, either idiopathic or associated with respiratory diseases such as COPD, asthma, cystic fibrosis, cancer, or gastrointestinal disturbances such as gastro-oesophageal reflux.

VR-1 antagonists may also have therapeutic benefit in inflammatory skin disorders, for example psoriasis and eczema, or itch of non-specific origin; contact dermatitis and hypersensitivity; autoimmune or inflammatory diseases, including Crohn's disease, ulcerative colitis and Gullian Barre Syndrome; multiple chemical sensitivity; neurological diseases like anxiety, panic disorders, depression, schizophrenia, cognition, Parkinson's Disease and Alzheimer's Disease; hair loss; diabetes; obesity and obesity-related diseases; as anti-spasmodics, e.g. for the treatment of spasm of the gastrointestinal tract or uterus; for the therapy of septic shock, e.g. as anti-hypovolaemic and I or anti hypotensive agents; and cerebral oedema.

Synergistic combinations of a VR-1 antagonist and an NSAID described by the invention are particularly useful as analgesics for treating or preventing pain. They may be used to improve the condition of a host, typically of a human being, suffering from pain. They may be employed to alleviate pain in a host. Thus, the combinations of the invention may be used as an analgesic to treat acute pain such as musculoskeletal pain, post operative pain and surgical pain, chronic pain such as chronic inflammatory pain (e.g. rheumatoid arthritis (RA) and osteoarthritis (OA), neuropathic pain (e.g. post herpetic neuralgia (PHN), trigeminal neuralgia, neuropathies associated with diabetes and sympathetically maintained pain) and pain associated with cancer and fibromyalgia. The combinations of the invention may also be used in the treatment or prevention of migraine and/or pain associated with migraine, tension headache and cluster headaches and pain associated with Functional Bowel Disorders (e.g. Irritable Bowel Syndrome), non cardiac chest pain and non ulcer dyspepsia. Synergistic combinations of a VR-1 antagonist and an NSAID, such as a COX-2 inhibitor, may also have particular use in the treatment of UI and diseases involving inflammation, for example inflammatory airways disorders and gastro-oestophageal reflux disease.

Suitable physiologically acceptable salts according to the invention include acid addition salts formed with inorganic acids such as hydrochlorides, hydrobromides, phosphates and sulphates and with organic acids, for example tatrates, maleates, fumarates, succinates and sulfonates.

Suitable vanilloid receptor (VR-1) antagonists include, but are not limited to, the examples and generic descriptions found in the following publications, hereby incorporated by reference in their entirety; co-pending GB Patent Applications GB 0303464.2, GB 0305291.7, GB 0305290.9, GB 0305165.3, GB 0305426.9, GB 0305285.9, GB 0305163.8 and GB 0316554.5; US 20030158188; US 20030158198; US 20040157845; US 20040157849; US 20040209884; US 20050009841; US 20050080095; US 20050085512; WO 02008221; WO 02030956; WO 02072536; WO 02076946; WO 02090326; WO 03006019; WO 03014064; WO 03022809; WO 03029199; WO 03049702; WO03053945; WO03055484; WO03055484; WO 03055848; WO 03062209; WO 03066595; WO 03068749; WO 03070247; WO 03074520; WO 03080578; WO 03093236; WO 03095420; WO 03097586; WO 03097670; WO 03099284; WO 04002983; WO 04007459; WO 04007495; WO 04011441; WO 04014871; WO 04024710; WO 04028440;

WO 04029031; WO 04029044; WO 04033435; WO 04035533; WO 04035549; WO 04046133; WO 04052845; WO 04052846; WO 04054582; WO 04055003; WO 04055004; WO 04056774; WO 04058754; WO 04072020; WO 04072069; WO 04074290; WO 04078101; WO 04078744; WO 04078749; WO 04089877; WO 04089881; WO 04096784; WO 04099177; WO 04100865; WO 04103281; WO 04108133; WO 04110986; WO 04111009; WO 05003084; WO 05004866; WO 05007646; WO 05007648; WO 05007652; WO 05009977; WO 05009980; WO 05009982; WO 05009987; WO 05009988; WO 05012287; WO 05014580; WO 05016915; WO 05016922; WO 05030753; WO 05030766; WO 05032493; WO 05033105; WO 05035471; WO 05028445; WO 05033105; US 2005080095; WO 05040121; WO 05051390; US 20050277643; U.S. Pat. No. 7,015,233; WO 06031852; WO 06033620; WO 06033620; WO 06038041; WO 06047279; WO 06038041; WO 06038871; WO 06038871; WO 06042289; WO 06044527; WO 06047492; WO 06045498; U.S. Pat. No. 7,037,927; US 20060100460; US 20060100245; US 20060111337; WO 2006058338; WO 2006062981; US 20060128689; WO 2006063178; US 20060128704; US 20060128755; US 20060135505; US 20060128704; WO 2006065872; WO 2006065646; U.S. Pat. No. 7,067,553(B2); WO 2006068593; WO 2006068592; WO 2006068618; U.S. Pat. No. 7,071,335; US 20060148814(A1); WO 2006071538; WO 2006072736; WO 2006076646(A2); WO 2006078907(A1); WO 2006078992(A2); WO 2006081388(A2); WO 2006080821; US 2006089311(A1); US 2006183745; WO 2006093832(A2); US 20060194805(A1); US 2006205773 (A1); WO 2006095263(A1); WO 2006094627(A2); WO 2006097817(A1); WO 2006098554; WO 2006101318; WO 2006101321; WO 2006102645; WO 2006100520; WO 2006103503; WO 2006105971; US 20060235036; WO 2006111346; US 20060240097; US 2006241296; WO 2006115168; WO 2006122250; US 2006120481(A2); US 2006122200(A1); WO 2006122769; WO 2006122770; WO 2006122771(A2); WO 2006122772(A2); WO 2006122773(A1); WO 2006122776(A1); WO 2006122777(A2); WO 2006122799 (A1); WO 2006124753(A2); US 20060270682(A1); US 20060270682(A1); WO 2006125276(A1); WO 2006136245 (A1); WO 2007009798(A2); WO 2007010383(A1); WO 2007010138(A2).

Exemplary VR1 antagonists include those compounds generically and specifically disclosed in International Patent Application, Publication Number WO 02/076946 (Novartis AG), which discloses compounds of formula (I):

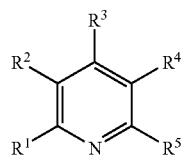
(I)

wherein
$R^1$ and $R^2$ together are —NH—C(SR$^6$)=N—C(O)—, —NR$^7$—C(R$^8$)=N—C(O)—, —N=C(SR$^9$)—NR$^{10}$—C(O)—, —NR$^{11}$—X—NR$^{12}$C(O)—, —NH—X—NH—, —NH—X—N=C(R$^{13}$)—, —NH—X—NH—CH$_2$—, —N=Z—NH—, —N=Z—NH—CH$_2$—, —N=Z—NH—C(O)— and —N=Z—N=C(R$^{14}$)—, wherein X is C(O), C(S) or C(O)—C(O); Z is N or CR$^{15}$, R$^6$ is $C_1$-$C_4$alkyl; R$^7$ and R$^8$ are each independently hydrogen, $C_1$-$C_4$alkyl, $C_3$-$C_8$cycloalkyl or form together with the adjacent atoms a 5 or 6 membered heterocyclic ring; R$^9$ and R$^{10}$ together are $C_1$-$C_4$alkylene; R$^{11}$ is hydrogen; $C_1$-$C_4$alkyl; $C_1$-$C_4$alkyl substituted by C(O)OC$_1$-$C_4$alkyl; or phenyl substituted by $C_1$-$C_4$alkyl; R$^{12}$ is hydrogen, NH$_2$; $C_1$-$C_4$alkyl; or phenyl substituted by $C_1$-$C_4$alkyl; R$^{13}$ is hydrogen, halogen, NH$_2$ or $C_1$-$C_4$alkoxy; R$^{14}$ is hydrogen, hydroxy, halogen, NH$_2$, $C_1$-$C_4$alkyl or $C_1$-$C_4$alkoxy; and R$^{15}$ is hydrogen, halogen, $C_1$-$C_4$alkyl, $C_1$-$C_4$alkoxy or SCH$_2$C(O)OC(CH$_3$)$_3$;
$R^3$ is hydrogen; OH; CN; $C_1$-$C_6$alkyl; phenyl; or C(O)OC$_1$-$C_4$alkyl;
$R^4$ is hydrogen; halogen; NH$_2$; CN; $C_1$-$C_6$alkyl; $C_1$-$C_6$alkyl substituted by OH; phenyl;
phenyl substituted by OH, halogen, $C_1$-$C_6$alkyl, $C_1$-$C_6$haloalkyl or $C_1$-$C_6$alkoxy; benzyl;
benzoyl substituted by OH; or C(O)OC$_1$-$C_6$alkyl; 5 or 6 membered aromatic or aliphatic heterocyclic ring;
$R^5$ is hydrogen; OH; NH$_2$; halogen; $C_1$-$C_6$alkyl; $C_1$-$C_6$alkyl substituted by halobenzyl;
$C_3$-$C_6$cycloalkyl; phenyl; pyridinyl; NHC$_1$-$C_4$alkyl; or N=CHN(C$_1$-$C_4$alkyl)$_2$;
with the proviso that compounds of formula I are not pyrido[3,2-d]pyrimidine-2,4(1H,3H)-dione and 6-chloro-2-methyl-4-oxo-pyrido[3,2-d]pyrimidine;
in free base or acid addition salt form. Preferred compounds are referred to as Examples 1, 2, 1.1-1.5, 2.1-2.16 and 3.1-3.6, particularly Example 2.

Further exemplary VR1 antagonists include those compounds generically and specifically disclosed in International Patent Application Publication Number WO2005120510, which discloses compounds of formula (II):

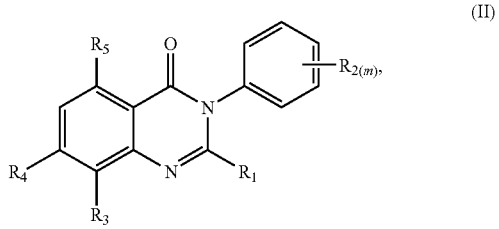

wherein
$R_1$ is $C_1$-$C_6$alkyl, ($C_1$-$C_6$alkyl)$C_1$-$C_6$alkyl, di-($C_1$-$C_6$alkyl) $C_1$-$C_6$alkyl, $C_3$-$C_6$cycloalkyl, ($C_1$-$C_6$alkyl)amino or di-($C_1$-$C_6$alkyl)amino;
each $R_2$, independently, is halogen, $C_1$-$C_6$alkyl, halogen-substituted $C_1$-$C_6$alkyl, hydroxy$C_1$-$C_6$alkyl, cyano or a group —C(=O)—$R_{2a}$, where $R_{2a}$ is $C_1$-$C_6$alkyl;
$R_3$ is hydrogen, halogen, $C_1$-$C_6$alkyl, $C_2$-$C_6$alkenyl, $C_2$-$C_6$alkynyl, hydroxy, hydroxy-substituted $C_1$-$C_6$alkyl, $C_1$-$C_6$alkoxy, $C_3$-$C_6$cycloalkyl, cyano, —C(=O)H, phenyl, ($C_3$-$C_6$cycloalkyl)$C_1$-$C_6$alkoxy, ($C_1$-$C_6$alkoxycarbonylamino)$C_1$-$C_6$alkoxy or ($C_1$-$C_6$alkylcarbonylamino)$C_1$-$C_6$alkoxy;
$R_4$ is hydroxy, esterified hydroxy, etherified hydroxy, amino, ($C_1$-$C_6$alkyl)amino, a group

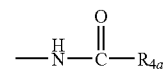

or a group,

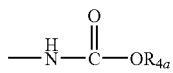

where $R_{4a}$ is $C_1$-$C_6$alkyl or halogen-substituted $C_1$-$C_6$alkyl, or a group

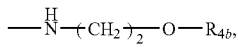

where $R_{4b}$ is benzyl or phenylethyl;
$R_5$ is hydrogen or hydroxy; and
m is 1 or 2,
in free form or in salt form, and, where possible, in acid addition salt form, as a vanilloid antagonist. Preferred compounds are referred to as Examples 1 to 28 and Examples 29.1 to 29.54, particularly Example 29.31.

Further suitable vanilloid receptor (VR-1) antagonists are (2R)-4-(3-chloropyridin-2-yl)-2-methyl-N-[4-trifluoromethyl)phenyl]piperazine-1-carboxamide (Example 20, WO 02/08221) and N-(2-Bromophenyl)-N'-[((R)-1-(5-trifluoromethyl-2-pyridyl) pyrrolidin-3-yl)]urea (Example 1, WO 03/022809).

In a preferred aspect of the invention there is provided a synergistic combination of a compound selected from 7-tert.-Butyl-6-(4-chlorophenyl)-2-thioxo-2,3-dihydro-1H-pyrido[2,3-d]pyrimidin-4-one and 4-(7-Hydroxy-2-isopropyl-4-oxo-4H-quinazolin-3-yl)-benzonitrile, or a pharmaceutically acceptable salt or solvate thereof, and an NSAID, such as a COX-2 inhibitor, or a pharmaceutical acceptable derivative thereof.

The above-mentioned patent applications describe in relation to the vanilloid VR-1 antagonists they disclose both suitable methods for their preparation and doses for their administration.

Suitable NSAIDS for use according to the invention include: naproxen, fenbufen, fenoprofen, flurbiprofen, ketoprofen, dexketoprofen, tiaprofenic acid, azapropazone, diclofenac, aceclofenac, diflunisal, indomethacin, ketorolac, mefenamic acid, nabumetone, phenylbutazone, piroxicam, sulindac, tenoxicam, tolfenamic acid, oxaprozin, ibuprofen and COX-2 selective inhibiting compounds (herein referred to as "COX-2 inhibitors").

It will be appreciated that the present invention relates to the use of a synergistic combination of any compound having vanilloid receptor VR-1 antagonist known in the art particularly in conjunction with any compound having COX-2 inhibitor activity known in the art.

A variety of COX-2 inhibitors have been described in the art, for example those mentioned in the following patent applications:
AU9719132 CA2164559 CA2180624 EP-799823
 EP-846689
EP-863134 FR2751966GB2283745 GB2319772
 GB2320715
JP08157361 U.S. Pat. No. 5,510,368 U.S. Pat. No. 5,681,842
 U.S. Pat. No. 5,686,460 U.S. Pat. No. 5,776,967
U.S. Pat. No. 5,783,597 U.S. Pat. No. 5,824,699 U.S. Pat. No. 5,830,911 U.S. Pat. No. 5,859,036 U.S. Pat. No. 5,869,524WO94/13635
WO94/20480WO94/26731WO95/00501WO952/1817
WO96/03385 WO96/03387 WO96/06840 WO96/09293
 WO96/09304 WO96/13483
WO96/16934 WO96/19462 WO96/19463 WO96/19469WO96/21667 WO96/23786
WO96/24584 WO96/24585 WO96/25405 WO96/26921
 WO96/31509 WO96/36617
WO96/36623 WO96/37467
WO96/37469WO96/38418 WO96/38442WO96/40143
 WO97/03953
 WO97/09977 WO97/13755 WO97/13767 WO97/14691
WO97/16435
WO97/25045 WO97/25046 WO97/25047 WO97/25048
 WO97/27181 WO97/28120
WO97/28121 WO97/30030 WO97/34882 WO97/36863
WO97/37984 WO97/38986 WO97/40012 WO97/46524
 WO97/46532
WO98/03484 WO98/04527 WO98/06708 WO98/06715
 WO98/07425 WO98/11080
WO98/15528 WO98/21195 WO98/22442 WO98/28292
WO98/29382 WO98/41511 WO98/41516 WO98/43966
 WO98/45294
WO98/46594 WO98/46611 WO98/47890 WO98/51667
 WO98/57924
WO99/01455 WO99/05104 WO99/10331 WO99/10332
 WO99/11605
WO99/12930 WO99/14194 WO99/14195 WO99/14205
 WO99/15505
ZA9704806 ZA9802828 all incorporated herein by reference as if set forth fully herein. The above applications also describe, in relation to the COX-2 inhibitors they disclose, both suitable methods for their preparation and doses for their administration.

Suitable COX-2 inhibitors for use according to the invention include: 2-[(2-chloro-6-fluorophenyl)amino]-5-methylphenyl (lumiracoxib), 2-(4-ethoxy-phenyl)-3-(4-methanesulfonyl-phenyl)-pyrazolo[1,5-b]pyridazine, CDC-501, celecoxib, COX-189, 4-(2-oxo-3-phenyl-2,3-dihydrooxazol-4-yl)benzenesulfonamide, CS-179, CS-502,D-1367, darbufelone, DFP, DRF-4367, etodolac, flosulide, JTE-522 (4-(4-cyclohexyl-2-methyl-5-oxazolyl)-2-fluorobenzenesulfonamide), L-745337, L-768277, L-776967, L-783003, L-791456, L-804600, meloxicam, MK663 (etoricoxib), nimesulide, NS-398, parecoxib, 1-Methylsulfonyl-4-(1,1-dimethyl-4-(4-fluorophenyl)cyclopenta-2,4-dien-3-yl)benzene,4-(1,5-Dihydro-6-fluoro-7-methoxy-3-(trifluoromethyl)-(2)-benzothiopyran o (4,3-c)pyrazol-1-yl)benzenesulfonamide, 4,4-dimethyl-2-phenyl-3-(4-methylsulfonyl)phenyl)cyclobutenone, 4-Amino-N-(4-(2-fluoro-5-trifluoromethyl)-thiazol-2-yl)-benzene sulfonamide, 1-(7-tert-butyl-2,3-dihydro-3,3-dimethyl-5-benzo-furanyl)-4-cyclopropylbutan-1-one, Pharmaprojects No. 6089 (Kotobuki Pharmaceutical), rofecoxib, RS-113472, RWJ-63556, S-2474, S-33516, SC-299, SC-5755, valdecoxib, UR-8877, UR-8813, UR-8880.

Preferred COX-2 inhibitors for use according to the invention include: lumiracoxib, celecoxib, rofecoxib, valdecoxib, parecoxib,4-(4-cyclohexyl-2-methyl-5-oxazolyl)-2-fluorobenzenesulfonamide (JTE-522), MK663, nimesulide, flosulide, DFP and 2-(4-ethoxy-phenyl)-3-(4-methanesulfonyl-phenyl)-pyrazolo[1,5-b]pyridazine, and their physiologically acceptable salts or solvates.

More preferred COX-2 inhibitors for use according to the invention are lumiracoxib, celecoxib, rofecoxib, valdecoxib, parecoxib, 4-(4-cyclohexyl-2-methyl-5-oxazolyl)-2-fluorobenzenesulfonamide (JTE-522) and 2-(4-ethoxy-phenyl)-3-(4-methanesulfonyl-phenyl)-pyrazolo[1,5-b]pyridazine, and their physiologically acceptable salts or solvates.

A particularly preferred COX-2 inhibitor for use according to the invention is lumiracoxib (Prexige) and its physiologically acceptable salts or solvates.

A further particularly preferred COX-2 inhibitor for use according to the invention is 2-(4-ethoxy-phenyl)-3-(4-methanesulfonyl-phenyl)-pyrazolo[1,5-b]pyridazine and its physiologically acceptable salts or solvates. Particularly interesting as pharmaceutically acceptable derivatives are modified at the benzenesulfonamide function to provide metabolically labile benzenesulfonamides. Acylated benzenesulphonamide derivatives are of especial interest.

A further particularly preferred COX-2 inhibitor for use according to the invention is rofecoxib and its physiologically acceptable salts or solvates.

According to a further aspect of the invention there is provided a synergistic combination of a compound selected from lumiracoxib, celecoxib, rofecoxib, valdecoxib, parecoxib,4-(4-cyclohexyl-2-methyl-5-oxazolyi)-2-fluorobenzenesulfonamide (JTE-522) and 2-(4-ethoxy-phenyl)-3-(4-methanesulfonyl-phenyl)-pyrazolo[1,5-b]pyridazine, or a pharmaceutically acceptable salt or solvate thereof, and a vanilloid receptor VR-1 antagonist, or a pharmaceutically acceptable salt or solvate thereof.

According to a further aspect of the invention there is provided a synergistic combination of a compound selected from 7-tert.-Butyl-6-(4-chlorophenyl)-2-thioxo-2,3-dihydro-1H-pyrido[2,3-d]pyrimidin-4-one and 4-(7-Hydroxy-2-isopropyl-4-oxo-4H-quinazolin-3-yl)-benzonitrile, or a pharmaceutically acceptable salt or solvate thereof, and a compound selected from lumiracoxib, celecoxib, rofecoxib, valdecoxib, parecoxib,4-(4-cyclohexyl-2-methyl-5-oxazolyi)-2-fluorobenzenesulfonamide (JTE-522) and 2-(4-ethoxy-phenyl)-3-(4-methanesulfonyl-phenyl)-pyrazolo[1,5-b]pyridazine, or a pharmaceutically acceptable salt or solvate thereof.

Compounds for use according to the invention may be administered simultaneously or sequentially and, when administration is sequential, either the vanilloid receptor VR-1 antagonist or the NSAID, such as a COX-2 inhibitor, may be administered first.

When administration is simultaneous, the combination may be administered either in the same or different pharmaceutical composition.

Compounds for use according to the invention may be administered as the raw material but the active ingredients are preferably provided in the form of pharmaceutical formulations.

The active ingredients may be used either as separate formulations or as a single combined formulation. When combined in the same formulation it will be appreciated that the two compounds must be stable and compatible with each other and the other components of the formulation. Therefore, pharmaceutical formulations comprising a combination as defined above together with a pharmaceutical acceptable diluent or carrier comprise a further aspect of the invention. When formulated separately they may be provided in any convenient formulation, conveniently in such manner as are known for such compounds in the art.

Accordingly in a further aspect of the invention there is provided a pharmaceutical composition which comprises a synergistic combination of a vanilloid receptor VR-1 antagonist or a pharmaceutical acceptable derivative thereof and an NSAID, such as a COX-2 inhibitor, or a pharmaceutically acceptable derivative thereof, and a suitable carrier or excipient, formulated for administration by any convenient route.

The above mentioned published documents, including patent applications and patents, are incorporated herein by reference as if each individual publication was specifically and fully set forth herein.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) or in a form suitable for administration by inhalation or insufflation administration, although the most suitable route may depend upon for example the condition and disorder of the recipient. The formulations may conveniently be presented in unit dosage form and may be prepared by any of the methods well known in the art of pharmacy. All methods include the step of bringing into association the compounds ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation. Preferably such compositions will be formulated for oral administration.

It will be appreciated that when the two active ingredients are administered independently, each may be administered by different means.

Formulations suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion.

The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a other conventional excipients such as binding agents, (for example, syrup, acacia, gelatin, sorbitol, tragacanth, mucilage of starch, polyvinylpyrrolidone) or hydroxymethyl cellulose or hydroxymethyl cellulose fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

For topical administration to the epidermis, the compounds may be formulated as creams, gels, ointments or lotions or as a transdermal patch.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For intranasal administration the compounds of the invention may be used, for example as a liquid spray, as a powder or in the form of drops.

For administration by inhalation the compounds according to the invention are conveniently delivered in the form of an aerosol spray presentation from pressurised packs or a nebuliser, with the use of a suitable propellant, e.g. 1,1,1,2-trifluoroethane (HFA 134A) and 1,1,1,2,3,3,3,-heptapropane (HFA 227), carbon dioxide or other suitable gas. In the case of a pressurised aerosol the dosage until may be determined by providing a valve to deliver a metered amount. Capsules and cartridges of e.g. gelatin for use in an inhaler or insufflator may be formulated containing a powder mix of a compound of the invention and a suitable powder base such as lactose or starch.

In addition to the ingredients particularly mentioned above, the formulations may include other agents conventional in the art having regard to the type of formulation in question, for example those suitable for oral administration may include flavouring agents.

It will be appreciated by those skilled in the art that reference herein to treatment extends to prophylaxis as well as the treatment of established diseases or symptoms.

Pharmaceutical compositions according to the invention may be prepared by conventional techniques. When combined in the same formulation for example, the vanilloid VR-1 antagonist or a pharmaceutically acceptable salt or solvate thereof and an NSAID, such as a COX-2 inhibitor, or a pharmaceutically acceptable salt or solvate thereof may be admixed together, if desired, with suitable excipients. Tablets may be prepared, for example, by direct compression of such a mixture. Capsules may be prepared, for example by filling the blend together with suitable excipients into gelatin capsules, using a suitable filling machine.

Compositions for use according to the invention may, if desired, be presented in a pack or dispenser device which may contain one or more unit dosage forms containing the active ingredients. The pack may, for example, comprise metal or plastic foil, such as a blister pack. Where the compounds are intended for administration as two separate compositions these may be presented, for example, in the form of a twin pack.

Pharmaceutical compositions may also be prescribed to the patient in "patient packs" containing the whole course of treatment in a single package, usually a blister pack.

Patient packs have an advantage over traditional prescriptions, where a pharmacists divides a patients supply of a pharmaceutical from a bulk supply, in that the patient always has access to the package insert contained in the patient pack, normally missing in traditional prescriptions. The inclusion of a package insert has been shown to improve patient compliance with the physicians instructions.

It will be understood that the administration of the combination of the invention by means of a single patient pack, or patients packs of each composition, including a package insert directing the patient to the correct use of the invention is a desirable additional feature of this invention.

According to a further aspect of the invention there is provided a patient pack comprising at least one active ingredient, of the combination according to the invention and an information insert containing directions on the use of the combination of the invention.

According to another aspect the invention provides a double pack comprising in association for separate administration of a vanilloid receptor VR-1 antagonist or pharmaceutical acceptable derivative thereof and an NSAID, such as a COX-2 inhibitor, or pharmaceutical acceptable derivative thereof.

It will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02-5000 mg per day, preferably 1-1500 mg per day. The desired dose may conveniently be presented in a single dose or as divided doses administered at appropriate intervals, for example as two, three, four or more sub-doses per day. The formulations according to the invention may contain between 0.1-99% of the active ingredient, conveniently from 30-95% for tablets and capsules and 3-50% for liquid preparations.

The combination of the present invention in a single dosage form is suitable for administration to any mammalian subject, preferably human. Administration may be once (o.d.), twice (b.i.d.) or three times (t.i.d.) daily, suitably b.i.d. or t.i.d., more suitably b.i.d, most suitably o.d.

Thus, as a further aspect of the present invention, there is provided a method of curative, prophylactic or palliative treatment of pain in a mammalian subject comprising once, twice or thrice, suitably twice or thrice, more suitably twice, most suitably once daily administration of a synergistic combination of a vanilloid receptor VR-1 antagonist and an NSAID, suitably a COX-2 inhibitor, or a pharmaceutically acceptable salt or solvate of both or either thereof.

Determining a synergistic interaction between one or more components, the optimum range for the effect and absolute dose ranges of each component for the effect may be definitively measured by administration of the components over different w/w ratio ranges and doses to patients in need of treatment. For humans, the complexity and cost of carrying out clinical studies on patients renders impractical the use of this form of testing as a primary model for synergy. However, the observation of synergy in one species can be predictive of the effect in other species and animal models exist, as described herein, to measure a synergistic effect and the results of such studies can also be used to predict effective dose and plasma concentration ratio ranges and the absolute doses and plasma concentrations required in other species by the application of pharmacokinetic/pharmacodynamic methods. Established correlations between animal models and effects seen in man suggest that synergy in animals can be demonstrated using acute or chronic inflammation-induced hyperalgesia or allodynia measurements (e.g. intraplantar CFA-induced mechanical hyperalgesia in rats). Because of plateau effects in such models, their value is best assessed in terms of synergistic actions that in neuropathic pain patients would translate to dose-sparing advantages. Other models in which existing agents used for the treatment of neuropathic pain give only a partial response are more suited to predict the potential of combinations acting synergistically to produce increased maximal efficacy at maximally tolerated doses of the two components.

Thus, as a further aspect of the present invention, there is provided a synergistic combination for human administration comprising vanilloid receptor VR-1 antagonist and an NSAID, suitably a Cox-2 inhibitor, or pharmaceutically acceptable salts or solvates thereof, in a w/w combination range which corresponds to the absolute ranges observed in a non-human animal model, preferably a rat model, primarily used to identify a synergistic interaction. Suitably, the ratio range in humans corresponds to a non-human range selected from between 1:50 to 50:1 parts by weight, 1:50 to 20:1, 1:50 to 10:1, 1:50 to 1:1, 1:20 to 50:1, 1:20 to 20:1, 1:20 to 10:1, 1:20 to 1:1, 1:10 to 50:1, 1:10 to 20:1, 1:10 to 10:1, 1:10 to 1:1, 1:1 to 50:1, 1.1 to 20:1 and 1:1 to 10:1. More suitably, the human range corresponds to a synergistic non-human range of 1:10 to 20:1 parts by weight. Preferably, the human range corresponds to a non-human range of the order of 1:1 to 10:1 parts by weight.

For humans, several experimental pain models may be used in man to demonstrate that agents with proven synergy in animals also have effects in man compatible with that synergy. Examples of human models that may be fit for this purpose include flare and inflammatory hyperalgesia following UVB exposure (Wilgus T A et al. (2002) Adv Exp Med Biol. 507, pp 85-92), the heat/capsaicin model (Petersen, K. L. & Rowbotham, M. C. (1999) NeuroReport 10, 1511-1516), the i.d capsaicin model (Andersen, O. L., Felsby, S., Nicolaisen, L., Bjerring, P., Jsesn, T. S. & Arendt-Nielsen, L. (1996) Pain 66, 51-62), including the use of repeated capsaicin trauma (Witting, N., Svesson, P., ArendtNielsen, L. & Jensen, T. S. (2000) Somatosensory Motor Res. 17, 5-12), and summation or wind-up responses (Curatolo, M. et al. (2000) Anesthesiology 93, 1517-1530). With these models, subjective assessment of pain intensity or areas of hyperalgesia may be used as endpoints, or more objective endpoints, reliant on electrophysiological or imaging technologies (such as functional magnetic resonance imaging) may be employed (Bomhovd, K., Quante, M., Glauche, V., Bromm, B., Weiller, C. & Buchel, C. (2002) Brain 125, 1326-1336). All such models require evidence of objective validation before it can be concluded that they provide evidence in man of supporting the synergistic actions of a combination that have been observed in animal studies.

For the present invention in humans, a suitable vanilloid receptor VR-1 antagonist:NSAID, suitably a Cox-2 inhibitor, ratio range is selected from between 1:50 to 50:1 parts by weight, 1:50 to 20:1, 1:50 to 10:1, 1:50 to 1:1, 1:20 to 50:1, 1:20 to 20:1, 1:20 to 10:1, 1:20 to 1:1, 1:10 to 50:1, 1:10 to 20:1, 1:10 to 10:1, 1:10 to 1:1, 1:1 to 50:1, 1:1 to 20:1 and 1:1 to 10:1, more suitably 1:10 to 20:1, preferably, 1:1 to 10:1.

Optimal doses of each component for synergy can be determined according to published procedures in animal models. However, in man (even in experimental models of pain) the cost can be very high for studies to determine the entire exposure response relationship at all therapeutically relevant doses of each component of a combination. It may be necessary, at least initially, to estimate whether effects can be observed that are consistent with synergy at doses that have been extrapolated from those that give optimal synergy in animals. In scaling the doses from animals to man, factors such as relative body weight/body surface area, relative absorption, distribution, metabolism and excretion of each component and relative plasma protein binding need to be considered and, for these reasons, the optimal dose ratio predicted for man (and also for patients) is unlikely to be the same as the dose ratio shown to be optimal in animals. However, the relationship between the two can be understood and calculated by one skilled in the art of animal and human pharmacokinetics. Important in establishing the bridge between animal and human effects are the plasma concentrations obtained for each component used in the animal studies, as these are related to the plasma concentration of each component that would be expected to provide efficacy in man. Pharmacokinetic/pharmacodynamic modeling (including methods such as isobolograms, interaction index and response surface modelling) and simulations may help to predict synergistic dose ratios in man, particularly where either or both of these components has already been studied in man.

It is important to ascertain whether any concluded synergy observed in animals or man is due solely to pharmacokinetic interactions. For example, inhibition of the metabolism of one compound by another might give a false impression of pharmacodynamic synergy. In animal studies with a vanilloid receptor VR-1 antagonist and an NSAID, repeated blood samples have been taken and it has been shown that, in accordance with the known pharmacokinetic properties of the agents, there is no evidence of any pharmacokinetic interaction when the compounds are administered at the doses that induced synergistic pain interactions. This proves that the synergy with respect to pain is pharmacodynamic, occurring subsequent to each of these agents interacting with their respective receptor and/or enzyme targets.

Thus, according to a further aspect of the present invention, there is provided a synergistic combination for administration to humans comprising vanilloid receptor VR-1 antagonist and an NSAID, suitably a Cox-2 inhibitor or pharmaceutically acceptable salts or solvates thereof, where the dose range of each component corresponds to the absolute synergistic ranges observed in a non-human animal model, preferably the rat model, primarily used to identify a synergistic interaction. Suitably, the dose range of vanilloid receptor VR-1 antagonist in human corresponds to a dose range of 1-20 mg/kg, more suitably 1-10 mg/kg, in the rat and the corresponding dose range for a vanilloid receptor VR-1 antagonist and an NSAID, suitably a Cox-2 inhibitor, is 0.1-10 mg/kg, more suitably 0.1-1 mg/kg.

Suitably, the dose of vanilloid receptor VR-1 antagonist for use in a human is in a range selected from 1-1200 mg, 1-500 mg, 1-100 mg, 1-50 mg, 1-25 mg, 500-1200 mg, 100-1200 mg, 100-500 mg, 50-1200 mg, 50-500 mg, or 50-100 mg, suitably 50-500 mg, b.i.d. or t.i.d., suitably t.i.d., and the dose of NSAID, suitably a Cox-2 inhibitor, is in a range selected from 1-500 mg, 1-200 mg, 1-100 mg, 1-50 mg, 1-25 mg, 10-100 mg, 10-50 mg or 10-25 mg, suitably 10-100 mg, b.i.d or t.i.d.

It will be apparent to the skilled reader that the plasma concentration ranges of the vanilloid receptor VR-1 antagonist and NSAID, suitably a Cox-2 inhibitor, combinations of the present invention required to provide a therapeutic effect depend on the species to be treated, and components used. It is possible, using standard PK/PD and allometric methods, to extrapolate from the plasma concentration values observed in an animal model a predicted dosing regime in a different species, particularly human. Thus, as a further aspect of the present invention, there is provided a synergistic combination for administration to humans comprising an vanilloid receptor VR-1 antagonist and an NSAID, suitably a Cox-2 inhibitor, where the plasma concentration range of each component corresponds to the absolute ranges observed in a non-human animal model, preferably the rat model, primarily used to identify a synergistic interaction.

It will further be apparent to those skilled in the art that the absolute doses required to achieve synergy will be dependent upon exposure to and efficacy of the vanilloid receptor VR-1 antagonist and NSAID, suitably a Cox-2 inhibitor, in the target tissue. Since this may vary between species, the synergistic concentrations observed between the combination of the invention may alternatively be expressed in terms of the sub-maximal:maximal dose ratio of each component when administered alone that in combination elicits a maximal therapeutic effect. For example, based on data obtained in a rodent species, the synergistic dosing regime to achieve maximal therapeutic effect in humans could be defined as the vanilloid receptor VR-1 antagonist concentration eliciting a x % therapeutic effect relative to the maximal, in combination with the concentration of NSAID eliciting y % therapeutic effect relative to the maximal.

It is possible, using standard PK/PD and allometric methods, to extrapolate the plasma concentration values observed in an animal model to predict the values in a different species, particularly human. Thus, as a further aspect of the present invention, there is provided a synergistic combination for administration to humans comprising an vanilloid VR-1 antagonist and an NSAID, suitably a Cox-2 inhibitor, where the plasma concentration range of each component corresponds to the absolute ranges observed in a non-human animal model, preferably a rat model, primarily used to identify a synergistic interaction.

Thus, an alternative aspect, the present invention provides a synergistic combination comprising a vanilloid VR-1 antagonist and an NSAID, suitably a Cox-2 inhibitor, or pharmaceutically acceptable salts or solvates thereof, where the plasma concentration range for the components comprises Cmax values of up to 20 µg/ml for the vanilloid VR-1 antagonist and up to 4 g/ml for an NSAiD, such as a COX-2 inhibitor, more suitably 0.005 g/ml to 4 g/ml.

It will be appreciated that the dose at which the vanilloid receptor VR-1 antagonist and the COX-2 inhibitor is administered will depend on the age and condition of the patient and the frequency and route of administration and will be at the ultimate discretion of the attendant physician. The active ingredients may conveniently be presented in unit dose form.

A vanilloid receptor VR-1 antagonist and an NSAID, such as a COX-2 inhibitor, for administration to man (of approximately 70 kg body weight) may conveniently be administered at doses within the normal range taught in the art at which the compounds are therapeutically effective.

For example, a proposed dose of the vanilloid receptor VR-1 antagonist for use according to the invention is 0.1 mg to 2 g, preferably 1 mg to 2 g, more preferably 1 mg to 500 mg per unit dose, expressed as the weight of free base. The unit dose may be administered in single or divided doses, for example, from 1 to 4 times per day.

For example, a proposed dose of the NSAID, such as a COX-2 inhibitor, for use according to the invention is 0.001 to 500 mg, preferably 0.01 to 100 mg, most preferably 0.05 to 50 mg, for example 0.5 to 25 mg per unit dose, expressed as the weight of the free base. The unit dose may be administered in single or divided doses, for example, from 1 to 4 times per day.

EXAMPLE 1

Suitable VR-1 compounds are as defined by formula (I) and specifically disclosed in Publication Number WO 02/076946, together with synthetic schemes for making them.

EXAMPLE 2

Further suitable VR-1 compounds are as defined by formula (II) and specifically disclosed in Publication Number WO2005120510, together with synthetic schemes for making them.

Biological Data

Experiments to determine whether a vanilloid receptor VR-1 antagonist, 4-(7-Hydroxy-2-isopropyl-4-oxo-4H-quinazolin-3-yl)-benzonitrile, in combination with an NSAID, diclofenac, behave synergistically to reverse acute inflammatory pain were conducted in male Wistar Han rats (180-200 g).

Mechanical hyperalgesia was determined after intraplantar injection of Freund's Complete Adjuvant (FCA) by measuring paw withdrawal thresholds to an increasing pressure stimulus applied to the hindpaw using an analgesymeter (Ugo-Basile) with a wedge-shaped probe (area 1.75 mm2) and a cut-off threshold of 180 g. The end point was taken as the first sign of pain response (struggling, vocalization or paw withdrawal). Paw withdrawal thresholds were measured in naïve animals prior to oral administration of vehicle or test compound. Inhibition of hyperalgesia was calculated according to the formula:

$$\% \text{ Inhibition} = \frac{\left(\begin{array}{c}\text{Mean naïve vehicle threshold} - \\ \text{Mean post caps vehicle threshold}\end{array}\right) - \left(\begin{array}{c}\text{naïve drug threshold} - \\ \text{post caps drug threshold}\end{array}\right)}{\left(\begin{array}{c}\text{Mean naïve vehicle threshold} - \\ \text{Mean post caps vehicle threshold}\end{array}\right)} \times 100$$

Figure 2:
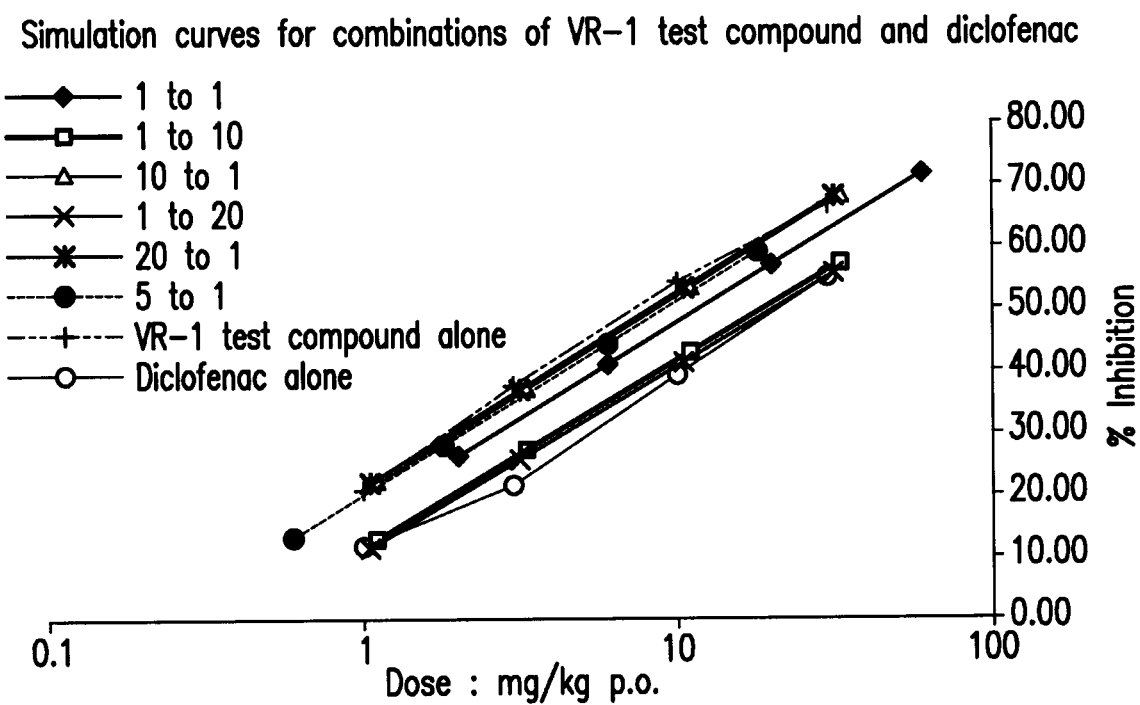
FIG. 2: Theoretical effect of combinations of 4-(7-Hydroxy-2-isopropyl-4-oxo-4H-quinazolin-3-yl)-benzonitrile (VR-1 test compound) and diclofenac on inhibition of acute mechanical hyperalgesia in the rat.

Dose response curves to oral administration of 4-(7-Hydroxy-2-isopropyl-4-oxo-4H-quinazolin-3-yl)-benzonitrile and diclofenac (given 1 h prior to hyperalgesia assessment) were determined in rats 4 h following 25 µl FCA administration (FIG. 1), from these two curves simulated dose-response curves for combination doses of 4-(7-Hydroxy-2-isopropyl-4-oxo-4H-quinazolin-3-yl)-benzonitrile and diclofenac were generated (following the method described in Tallarida et al (Life Sci 61: 417-425; see FIG. 2). Experiments were then performed to establish the dose response curves from the combination doses used in the simulations. Positive synergy would be evident where leftward shift of the dose response curve, with respect to the simulated curve, was seen.

Figure 3A:
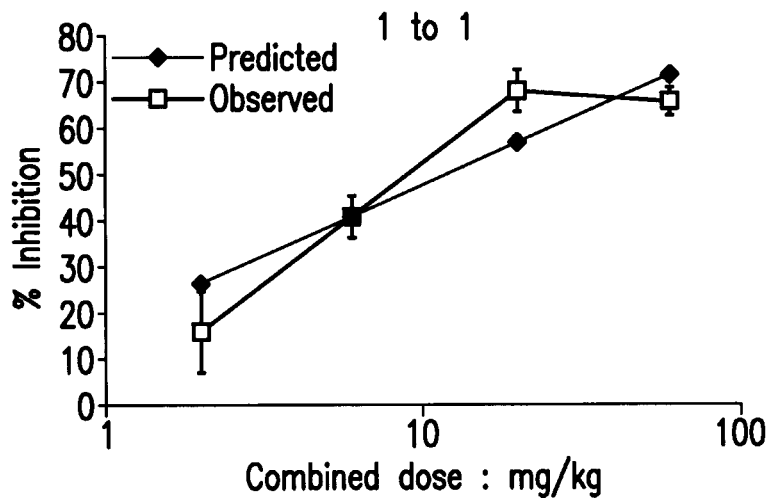
FIG. 3: Graphs showing the effect of combined doses of 4-(7-Hydroxy-2-isopropyl-4-oxo-4H-quinazolin-3-yl)-benzonitrile and diclofenac in ratios of 1:1, 10:1 and 5:1 on inhibition of acute inflammatory hyperalgesia in the rat. Also shown are theoretical curves derived from experimental dose response curves to 4-(7-Hydroxy-2-isopropyl-4-oxo-4H-quinazolin-3-yl)-benzonitrile and diclofenac when dosed alone.
Figure 3B:
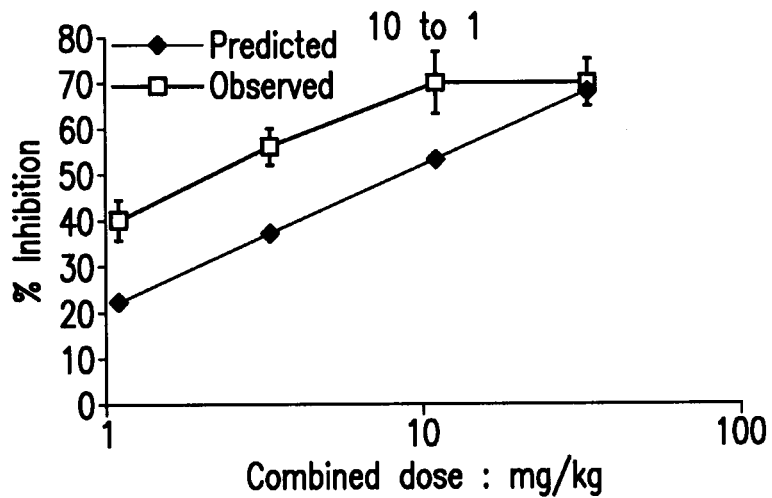
Figure 3C:
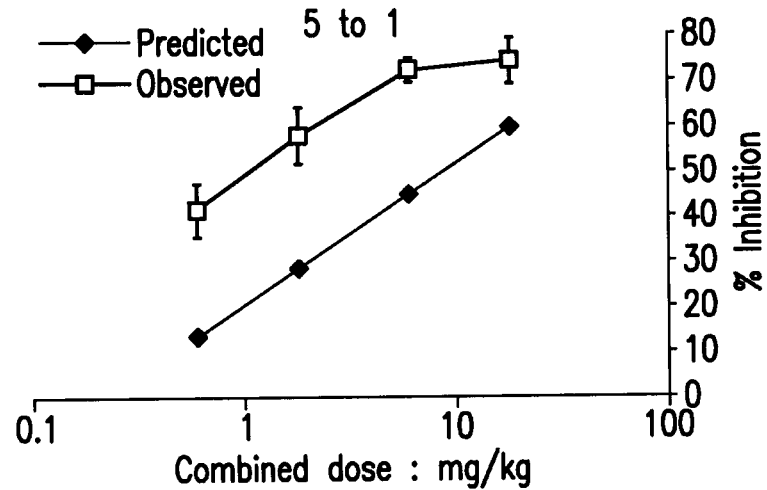

The combinations examined were (4-(7-Hydroxy-2-isopropyl-4-oxo-4H-quinazolin-3-yl)-benzonitrile to diclofenac) 1:1, 1:10, 10:1, 1:20; 20:1 & 5:1. Positive synergy was observed with dose combinations of 10:1 and 5:1 (see FIG. 3 for 5:1 experiment), synergism was confirmed by ANCOVA p=<0.05 in both cases. All other combinations tested did not produce synergy.

The present invention also provides the combination of a VR-1 receptor antagonist selected from Formula (I):

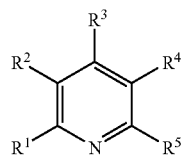

wherein
$R^1$ and $R^2$ together are —NH—C(SR$^6$)=N—C(O)—, —NR$^7$—C(R$^8$)=N—C(O)—, —N=C(SR$^9$)—NR$^{10}$—C(O)—, —NR$^{11}$—X—NR$^{12}$C(O)—, —NH—X—NH—, —NH—X—N=C(R$^{13}$)—, —NH—X—NH—CH$_2$—, —N=Z—NH—, —N=Z—NH—CH$_2$—, —N=Z—NH—C(O)— and —N=Z—N=C(R$^{14}$)—, wherein X is C(O), C(S) or C(O)—C(O); Z is N or CR$^{15}$, R$^6$ is C$_1$-C$_4$alkyl; R$^7$ and R$^8$ are each independently hydrogen, C$_1$-C$_4$alkyl, C$_3$-C$_8$cycloalkyl or form together with the adjacent atoms a 5 or 6 membered heterocyclic ring; R$^9$ and R$^{10}$ together are C$_1$-C$_4$alkylene; R$^{11}$ is hydrogen; C$_1$-C$_4$alkyl; C$_1$-C$_4$alkyl substituted by C(O)OC$_1$-C$_4$alkyl; or phenyl substituted by C$_1$-C$_4$alkyl; R$^{12}$ is hydrogen, NH$_2$; C$_1$-C$_4$alkyl; or phenyl substituted by C$_1$-C$_4$alkyl; R$^{13}$ is hydrogen, halogen, NH$_2$ or C$_1$-C$_4$alkoxy; R$^{14}$ is hydrogen, hydroxy, halogen, NH$_2$, C$_1$-C$_4$alkyl or C$_1$-C$_4$alkoxy; and R$^{15}$ is hydrogen, halogen, C$_1$-C$_4$alkyl, C$_1$-C$_4$alkoxy or SCH$_2$C(O)OC(CH$_3$)$_3$;

$R^3$ is hydrogen; OH; CN; C$_1$-C$_6$alkyl; phenyl; or C(O)OC$_1$-C$_4$alkyl;

$R^4$ is hydrogen; halogen; NH$_2$; CN; C$_1$-C$_6$alkyl; C$_1$-C$_6$alkyl substituted by OH; phenyl;
phenyl substituted by OH, halogen, C$_1$-C$_6$alkyl, C$_1$-C$_6$haloalkyl or C$_1$-C$_6$alkoxy; benzyl; benzoyl substituted by OH; or C(O)OC$_1$-C$_6$alkyl; 5 or 6 membered aromatic or aliphatic heterocyclic ring;

$R^5$ is hydrogen; OH; NH$_2$; halogen; C$_1$-C$_6$alkyl; C$_1$-C$_6$alkyl substituted by halobenzyl;

C$_3$-C$_6$cycloalkyl; phenyl; pyridinyl; NHC$_1$-C$_4$alkyl; or N=CHN(C$_1$-C$_4$alkyl)$_2$;

with the proviso that compounds of formula I are not pyrido[3,2-d]pyrimidine-2,4(1H,3H)-dione and 6-chloro-2-methyl-4-oxo-pyrido[3,2-d]pyrimidine; in free base or acid addition salt form; and formula (II):

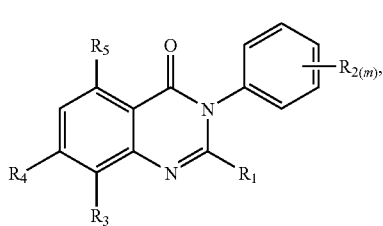

wherein
$R_1$ is C$_1$-C$_6$alkyl, (C$_1$-C$_6$alkyl)C$_1$-C$_6$alkyl, di-(C$_1$-C$_6$alkyl)C$_1$-C$_6$alkyl, C$_3$-C$_6$cycloalkyl, (C$_1$-C$_6$alkyl)amino or di-(C$_1$-C$_6$alkyl)amino;

each $R_2$, independently, is halogen, C$_1$-C$_6$alkyl, halogen-substituted C$_1$-C$_6$alkyl, hydroxyC$_1$-C$_6$alkyl, cyano or a group —C(=O)—R$_{2a}$, where R$_{2a}$ is C$_1$-C$_6$alkyl;

$R_3$ is hydrogen, halogen, C$_1$-C$_6$alkyl, C$_2$-C$_6$alkenyl, C$_r$C$_6$alkynyl, hydroxy, hydroxy-substituted C$_1$-C$_6$alkyl, C$_1$-C$_6$alkoxy, C$_3$-C$_6$cycloalkyl, cyano, —C(=O)H, phenyl, (C$_3$-C$_6$cycloalkyl)C$_1$-C$_6$alkoxy, (C$_1$-C$_6$alkoxycarbonylamino)C$_1$-C$_6$alkoxy or (C$_1$-C$_6$alkylcarbonylamino)C$_1$-C$_6$alkoxy;

$R_4$ is hydroxy, esterified hydroxy, etherified hydroxy, amino, (C$_1$-C$_6$alkyl)amino, a group

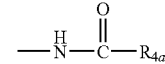

or a group,

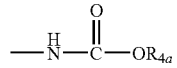

where $R_{4a}$ is C$_1$-C$_6$alkyl or halogen-substituted C$_1$-C$_6$alkyl, or a group

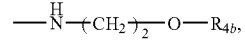

where $R_{4b}$ is benzyl or phenylethyl;
$R_5$ is hydrogen or hydroxy; and
m is 1 or 2,
in free form or in salt form;

and an antipyretic agent selected from acetaminophen, acetaminosalol, acetanilide, alclofenac, aminopyrine, aspirin, benorylate, benzydamine, bermoprofen, p-bromoacetanilide, bufexamac, bumadizon, calcium acetylsalicylate, chlorthenoxazin, clidanac, dipyrocetyl, dipyrone, epirizole, ibuprofen, imidazole salicylate, indomethacin, p-lactophenetide, lysine acetylsalicylate, magnesium acetylsalicylate, meclofenamic acid, morazone, naproxen, 5'-nitro-2'-propoxyacetanilide, phenacetin, phenocoll, phenyl acetylsalicylate, phenyl salicylate, pipebuzone, propacetamol, propyphenazone, ramifenazone, salacetamide, salicylamide O-acetic acid, salicylic acid, tetrandrine, tinoridine, aluminium bis(acetylsalicylate), aminochlorthenoxazin, dihydroxyaluminium acetylsalicylate, etersalate, isofezolac, nifenazone, phenicarbazide and phenopyrazone.

In one embodiment, there is provided a combination of a compound of formula (I) as defined above or a pharmaceutical acceptable derivative thereof and an antipyretic agent selected from acetaminophen, acetaminosalol, acetanilide, alclofenac, aminopyrine, aspirin, benorylate, benzydamine, bermoprofen, p-bromoacetanilide, bufexamac, bumadizon, calcium acetylsalicylate, chlorthenoxazin, clidanac, dipyrocetyl, dipyrone, epirizole, ibuprofen, imidazole salicylate, indomethacin, p-lactophenetide, lysine acetylsalicylate, magnesium acetylsalicylate, meclofenamic acid, morazone, naproxen, 5'-nitro-2'-propoxyacetanilide, phenacetin, phenocoll, phenyl acetylsalicylate, phenyl salicylate, pipebuzone, propacetamol, propyphenazone, ramifenazone, salacetamide, salicylamide O-acetic acid, salicylic acid, tetrandrine, tinoridine, aluminium bis(acetylsalicylate), aminochlorthenoxazin, dihydroxyaluminium acetylsalicylate, etersalate, isofezolac, nifenazone, phenicarbazide and phenopyrazone.

In a further embodiment, there is provided a combination of a compound of formula (II) as defined above or a pharmaceutical acceptable derivative thereof and an antipyretic agent selected from acetaminophen, acetaminosalol, acetanilide, alclofenac, aminopyrine, aspirin, benorylate, benzydamine, bermoprofen, p-bromoacetanilide, bufexamac, bumadizon, calcium acetylsalicylate, chlorthenoxazin, clidanac, dipyrocetyl, dipyrone, epirizole, ibuprofen, imidazole salicylate, indomethacin, p-lactophenetide, lysine acetylsalicylate, magnesium acetylsalicylate, meclofenamic acid, morazone, naproxen, 5'-nitro-2'-propoxyacetanilide, phenacetin, phenocoll, phenyl acetylsalicylate, phenyl salicylate, pipebuzone, propacetamol, propyphenazone, ramifenazone, salacetamide, salicylamide O-acetic acid, salicylic acid, tetrandrine, tinoridine, aluminium bis(acetylsalicylate), aminochlorthenoxazin, dihydroxyaluminium acetylsalicylate, etersalate, isofezolac, nifenazone, phenicarbazide and phenopyrazone.

The invention further provides a pharmaceutical composition comprising a VR-1 receptor antagonist or a pharmaceutical acceptable derivative thereof and an antipyretic agent or a pharmaceutical acceptable derivative thereof, as defined above, together with a pharmaceutically acceptable excipient.

According to another aspect of the invention, there is provided the use of a VR-1 receptor antagonist or a pharmaceutical acceptable derivative thereof and an antipyretic agent or a pharmaceutical acceptable derivative thereof, as defined above, for the manufacture of a medicament for the treatment of VR-1 mediated disorders, such as pain and the alleviation of symptoms associated thereof.

As a suitable aspect of the present invention, the compounds of formula (II) or a pharmaceutical acceptable derivative thereof and the preferred compounds specifically disclosed in WO2005120510 are useful in the treatment of obesity and obesity related disorders selected from: type 2 diabetes; type I diabetes; cardiovascular disease; hypertension; cancer, including but not limited to colon cancer, rectal cancer, colorectal cancer, pancreatic cancer, esophageal cancer, breast cancer, prostate cancer, uterine cancer, kidney cancer, endometrial cancer, gall bladder cancer, thyroid cancer, liver cancer, cervical cancer, ovarian cancer, stomach cancer, non-Hodgkin's lymphoma and multiple myeloma; and reproductive disorders, including but not limited to polycystic ovarian syndrome (PCO), infertility, and impotency or erectile dysfunction. The use of vanilloid antagonists in the treatment of obesity and related diseases is described in WO2006007851.

A further aspect of the invention provides a combination of a compound of formula (II) as defined above or a pharmaceutical acceptable derivative thereof and an anti-obesity agent selected from the group consisting of a 5HT (serotonin) transporter inhibitor, a NE (norepinephrine) transporter inhibitor, a ghrelin antibody, a ghrelin antagonist, a H3 (histamine H3) antagonist/inverse agonist, a MCH1R (melanin concentrating hormone 1R) antagonist, a MCH2R (melanin concentrating hormone 2R) agonist/antagonist, a NPY1 (neuropeptide Y Y1) antagonist, a NPY2 (neuropeptide Y Y2) agonist, a NPY5 (neuropeptide Y Y5) antagonist, leptin, a leptin derivative, an opioid antagonist, an orexin antagonist, a BRS3 (bombesin receptor subtype 3) agonist, a CCK-A (cholecystokinin-A) agonist, a CNTF (ciliary neurotrophic factor), a CNTF derivative, a GHS (growth hormone secretagogue receptor) agonist, 5HT2c (serotonin receptor 2c) agonist, a Mc3r (melanocortin 3 receptor) agonist, a Mc4r (melanocortin 4 receptor) agonist, a monoamine reuptake inhibitor, a serotonin reuptake inhibitor, topiramate, phytopharm compound 57, an ACC2 (acetyl-CoA carboxylase-2) inhibitor, a β3 (beta adrenergic receptor 3) agonist, a FAS (fatty acid synthase) inhibitor, a PDE (phosphodiesterase) inhibitor, a thyroid hormone, B agonist, an UCP-1 (uncoupling protein 1), 2, or 3 activator, an acyl-estrogen, a glucocorticoid antagonist, an 11O HSD-1 (11-beta hydroxy steroid dehydrogenase type 1) inhibitor, a lipase inhibitor, a fatty acid transporter inhibitor, a dicarboxylate transporter inhibitor, a glucose transporter inhibitor and a phosphate transporter inhibitor.

In an embodiment of the invention, there is provided a compound specifically disclosed in WO2005120510 in combination with an anti-obesity agent as defined above.

The invention claimed is:

1. A synergistic combination of 4-(7-hydroxy-2-isopropyl-4-oxo-4H-quinazolin-3-yl)-benzonitrile and diclofenac, or a pharmaceutically acceptable salt of either or both compounds thereof, wherein the ratio of 4-(7-hydroxy-2-isopropyl-4-oxo-4H-quinazolin-3-yl)-benzonitrile to diclofenac is between 5:1 and 10:1.

2. A pharmaceutical composition comprising a synergistic combination according to claim 1 and a suitable carrier or excipient.

* * * * *